United States Patent
Cordonnier (10) Patent No.: US 11,083,586 B2
(45) Date of Patent: Aug. 10, 2021

(54) SYSTEMS AND METHODS FOR MULTI-PLANAR ORTHOPEDIC ALIGNMENT

(71) Applicant: CARLSMED, INC., Carlsbad, CA (US)

(72) Inventor: Michael J. Cordonnier, Carlsbad, CA (US)

(73) Assignee: Carlsmed, Inc., La Jolla, CA (US)

( * ) Notice: Subject to any disclaimer, the term of this patent is extended or adjusted under 35 U.S.C. 154(b) by 0 days.

(21) Appl. No.: 16/207,116

(22) Filed: Dec. 1, 2018

(65) Prior Publication Data

US 2019/0167435 A1 Jun. 6, 2019

Related U.S. Application Data

(60) Provisional application No. 62/594,510, filed on Dec. 4, 2017.

(51) Int. Cl.
*A61F 2/30* (2006.01)
*A61F 2/44* (2006.01)

(52) U.S. Cl.
CPC ........ *A61F 2/30942* (2013.01); *A61F 2/4455* (2013.01); *A61F 2/446* (2013.01);
(Continued)

(58) Field of Classification Search
CPC .... A61F 2/30942; A61F 2/4455; A61F 2/446; A61F 2/4465; A61F 2/447; A61B 34/20; A61B 34/25; A61B 34/30
See application file for complete search history.

(56) References Cited

U.S. PATENT DOCUMENTS

| 4,704,686 A | 11/1987 | Aldinger |
| 6,696,073 B2 | 2/2004 | Boyce et al. |

(Continued)

FOREIGN PATENT DOCUMENTS

| CN | 104318009 A | 1/2015 |
| CN | 104353121 A | 2/2015 |

(Continued)

OTHER PUBLICATIONS

Endo, Kenji et al. "Measurement of whole spine sagittal alignment using the SLOT radiography of the SONIALVISION safire series clinical application." Medical Now, No. 78; Aug. 2015, 4 pages.

(Continued)

*Primary Examiner* — Si Ming Ku
(74) *Attorney, Agent, or Firm* — Perkins Coie LLP (57) ABSTRACT

A method for designing a patient-specific implant includes obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide an additive manufacturing operation.

30 Claims, 9 Drawing Sheets

(52) U.S. Cl.
CPC ............ *A61F 2/447* (2013.01); *A61F 2/4465* (2013.01); *A61F 2002/30593* (2013.01); *A61F 2002/30943* (2013.01); *A61F 2002/30948* (2013.01); *A61F 2002/30952* (2013.01); *A61F 2002/30953* (2013.01); *A61F 2002/30985* (2013.01)

(56) References Cited

U.S. PATENT DOCUMENTS

| | | | |
|---|---|---|---|
| 6,772,026 | B2 | 8/2004 | Bradbury |
| 7,174,282 | B2 | 2/2007 | Hollister et al. |
| 7,799,077 | B2 | 9/2010 | Lang |
| 8,246,680 | B2 | 8/2012 | Betz |
| 8,265,949 | B2 | 9/2012 | Haddad |
| 8,275,594 | B2 | 9/2012 | Lin |
| 8,337,507 | B2 | 12/2012 | Lang |
| 8,394,142 | B2 | 3/2013 | Bertagnoli |
| 8,457,930 | B2 | 6/2013 | Shroeder |
| 8,556,983 | B2 | 10/2013 | Bojarski et al. |
| 8,644,568 | B1 | 2/2014 | Hoffman |
| 8,735,773 | B2 | 5/2014 | Lang |
| 8,758,357 | B2 | 6/2014 | Frey |
| 8,781,557 | B2 | 7/2014 | Dean |
| 8,843,229 | B2 | 9/2014 | Vanasse |
| 8,855,389 | B1 | 10/2014 | Hoffman |
| 8,870,889 | B2 | 10/2014 | Frey |
| 9,198,678 | B2 | 12/2015 | Frey et al. |
| 9,208,558 | B2 | 12/2015 | Dean |
| 9,445,907 | B2 | 9/2016 | Meridew |
| 9,542,525 | B2 | 1/2017 | Arisoy et al. |
| 9,642,633 | B2 | 5/2017 | Frey et al. |
| 9,693,831 | B2 | 7/2017 | Mosnier et al. |
| 9,707,058 | B2 | 7/2017 | Bassett |
| 9,757,245 | B2 | 9/2017 | O'Neil et al. |
| 9,775,680 | B2 | 10/2017 | Bojarski et al. |
| 9,782,228 | B2 | 10/2017 | Mosnier et al. |
| 9,993,341 | B2 | 6/2018 | Vanasse |
| 10,292,770 | B2 | 5/2019 | Ryan |
| 10,390,958 | B2 | 8/2019 | Maclennan |
| 10,463,433 | B2* | 11/2019 | Turner .................. G16H 50/50 |
| 10,517,681 | B2 | 12/2019 | Roh et al. |
| 10,902,944 | B1 | 1/2021 | Casey et al. |
| 2005/0049590 | A1 | 3/2005 | Alleyne et al. |
| 2006/0009780 | A1 | 1/2006 | Foley |
| 2007/0276501 | A1 | 11/2007 | Betz et al. |
| 2011/0301710 | A1 | 12/2011 | Mather et al. |
| 2012/0084064 | A1 | 4/2012 | Dzenis et al. |
| 2012/0191192 | A1 | 7/2012 | Park |
| 2012/0287238 | A1 | 11/2012 | Onishi |
| 2012/0296433 | A1* | 11/2012 | Farin .................. A61F 2/30771 623/17.16 |
| 2013/0211531 | A1* | 8/2013 | Steines ................ A61F 2/3859 623/20.35 |
| 2014/0072608 | A1 | 3/2014 | Karagkiozaki et al. |
| 2014/0081659 | A1 | 3/2014 | Nawana et al. |
| 2014/0086780 | A1 | 3/2014 | Miller |
| 2014/0164022 | A1 | 6/2014 | Reed et al. |
| 2014/0350614 | A1 | 11/2014 | Frey |
| 2016/0015465 | A1 | 1/2016 | Steines et al. |
| 2016/0074048 | A1 | 3/2016 | Pavlovskaia et al. |
| 2016/0117817 | A1 | 4/2016 | Seel |
| 2016/0143744 | A1 | 5/2016 | Bojarski et al. |
| 2016/0210374 | A1* | 7/2016 | Mosnier .................. G06F 30/00 |
| 2016/0217268 | A1 | 7/2016 | Otto et al. |
| 2016/0354039 | A1 | 12/2016 | Soto et al. |
| 2016/0378919 | A1 | 12/2016 | McNutt et al. |
| 2017/0000566 | A1 | 1/2017 | Gordon |
| 2017/0014169 | A1 | 1/2017 | Dean et al. |
| 2017/0035514 | A1 | 2/2017 | Fox et al. |
| 2017/0061375 | A1 | 3/2017 | Laster et al. |
| 2017/0068792 | A1 | 3/2017 | Reiner |
| 2017/0135706 | A1 | 5/2017 | Frey et al. |
| 2017/0143831 | A1 | 5/2017 | Varanasi et al. |
| 2017/0220740 | A1 | 8/2017 | D'Urso |
| 2017/0262595 | A1 | 9/2017 | Vorhis et al. |
| 2018/0168499 | A1 | 6/2018 | Bergold et al. |
| 2018/0168731 | A1 | 6/2018 | Reid et al. |
| 2018/0233222 | A1 | 8/2018 | Daley |
| 2018/0233225 | A1 | 8/2018 | Experton et al. |
| 2018/0250075 | A1 | 9/2018 | Cho |
| 2018/0303552 | A1 | 10/2018 | Ryan |
| 2018/0338841 | A1 | 11/2018 | Miller et al. |
| 2019/0029757 | A1 | 1/2019 | Roh et al. |
| 2019/0146458 | A1 | 5/2019 | Roh et al. |
| 2019/0201106 | A1 | 7/2019 | Siemionow |
| 2019/0262084 | A1 | 8/2019 | Roh et al. |
| 2019/0282367 | A1 | 9/2019 | Casey et al. |
| 2019/0321193 | A1 | 10/2019 | Casey et al. |
| 2020/0078180 | A1 | 3/2020 | Casey et al. |
| 2020/0085509 | A1 | 3/2020 | Roh et al. |
| 2020/0170802 | A1 | 6/2020 | Casey et al. |
| 2021/0059822 | A1 | 3/2021 | Casey et al. |

FOREIGN PATENT DOCUMENTS

| | | |
|---|---|---|
| CN | 204468348 U | 7/2015 |
| CN | 105796214 A | 7/2016 |
| WO | 2010151564 A1 | 12/2010 |
| WO | 2019112917 A1 | 6/2019 |

OTHER PUBLICATIONS

International Searching Authority, International Search Report and Written Opinion, PCT Patent Application PCT/US2018/063530, dated Feb. 12, 2019, 16 pages.

Pimenta, Dr. Luiz, "Current Surgical Strategies to Restore Proper Sagittal Alignment," Journal of Spine 2015, vol. 4, Issue 4, 2 pages.

International Search Report and Written Opinion for International Application No. PCT/US19/50885, dated Jan. 28, 2020 (21 pages).

International Search Report and Written Opinion for International Application No. PCT/US19/63855, dated Feb. 14, 2020 (15 pages).

U.S. Appl. No. 15/958,409, for Ryan, filed Apr. 21, 2017.

\* cited by examiner

FIG. 32

SYSTEMS AND METHODS FOR MULTI-PLANAR ORTHOPEDIC ALIGNMENT

INCORPORATION BY REFERENCE TO ANY PRIORITY APPLICATIONS

This application claims the benefit of priority to U.S. Provisional Patent Application No. 62/594,510, filed on Dec. 4, 2017, which is herein incorporated by reference in its entirety for all purposes. Priority is claimed pursuant to 35 U.S.C. § 119.

FIELD OF THE INVENTION

The field of the invention generally relates to patient-specific implants, including patient-specific orthopedic implants, and methods for designing and producing them.

BACKGROUND

Orthopedic implants are used to correct a variety of different maladies. Orthopedic surgery utilizing orthopedic implants may include one of a number of specialties, including: hand surgery, shoulder and elbow surgery, total joint reconstruction (arthroplasty), skull reconstruction, pediatric orthopedics, foot and ankle surgery, spine surgery, musculoskeletal oncology, surgical sports medicine, and orthopedic trauma. Spine surgery may encompass one or more of the cervical, thoracic, lumbar spine, or the sacrum, and may treat a deformity or degeneration of the spine, or related back pain, leg pain, or other body pain. Irregular spinal curvature may include scoliosis, lordosis, or kyphosis (hyper or hypo), and irregular spinal displacement may include spondylolisthesis. Other spinal disorders include osteoarthritis, lumbar degenerative disc disease or cervical degenerative disc disease, lumbar spinal stenosis or cervical spinal stenosis.

Spinal fusion surgery may be performed to set and hold purposeful changes imparted on the spine. Spinal fusion procedures include PLIF (posterior lumbar interbody fusion), ALIF (anterior lumbar interbody fusion), TLIF (transverse or transforaminal lumbar interbody fusion), or LLIF (lateral lumbar interbody fusion), including DLIF (direct lateral lumbar interbody fusion) or XLIF (extreme lateral lumbar interbody fusion).

One goal of interbody fusion is to grow bone between vertebra in order to seize (e.g., lock) the spatial relationships in a position that provides enough room for neural elements, including exiting nerve roots. An interbody implant device (interbody device, interbody implant, interbody cage, fusion cage, or spine cage) is a prosthesis used in spinal fusion procedures to maintain relative position of vertebra and establish appropriate foraminal height and decompression of exiting nerves. Each patient may have individual or unique disease characteristics, but most implant solutions include implants (e.g. interbody implants) having standard sizes or shapes (stock implants).

SUMMARY OF THE INVENTION

In one embodiment of the present disclosure, a method for designing a patient-specific implant includes obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide an additive manufacturing operation.

In another embodiment of the present disclosure, a method for designing a patient-specific implant includes obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide a subtractive manufacturing operation.

In still another embodiment of the present disclosure, a method for designing a patient-specific implant includes obtaining image data of a region of interest of the spine of a patient, measuring one or more geometric characteristic of the region of interest from the image data, comparing a measurement obtained for each member of a selected group of the one or more geometric characteristics to a mathematical rule associated with the particular geometric characteristic, creating a corrected value for any of the one or more geometric characteristics that do not conform with the associated mathematical rule, and generating three-dimensional implant geometry data configured to guide an additive manufacturing operation.

In yet another embodiment of the present disclosure, a method for designing a patient-specific implant includes obtaining image data of a region of interest of the spine of a patient, measuring one or more geometric characteristic of the region of interest from the image data, comparing a measurement obtained for each member of a selected group of the one or more geometric characteristics to a mathematical rule associated with the particular geometric characteristic, creating a corrected value for any of the one or more geometric characteristics that do not conform with the associated mathematical rule, and generating three-dimensional implant geometry data configured to guide a subtractive manufacturing operation.

In still another embodiment of the present disclosure, a method for designing a patient-specific implant includes obtaining or uploading computed tomography (CT) data from a spine of a subject, converting the computed tomography (CT) data into a three-dimensional image, selecting or indicating selected segments of the spine for applying surgical correction, applying one or more correction guidelines for the selected segments of the spine; determining whether the selected segments of the spine conform to the one or more correction guidelines, and generating three-dimensional implant geometry data configured to guide an automated manufacturing operation configured to produce an implant.

In yet another embodiment of the present disclosure, a computer system for designing a patient-specific implant includes at least one computer memory that is not a transitory signal, the at least one computer memory including instructions executable by at least one processor for obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide an additive manufacturing operation.

In still another embodiment of the present disclosure, a computer system for designing a patient-specific implant includes at least one computer memory that is not a transitory signal, the at least one computer memory including instructions executable by at least one processor for obtaining image data of a region of interest of the spine of a patient, measuring one or more geometric characteristic of the region of interest from the image data, comparing a measurement obtained for each member of a selected group of the one or more geometric characteristics to a mathematical rule associated with the particular geometric characteristic, creating a corrected value for any of the one or more geometric characteristics that do not conform with the associated mathematical rule, and generating three-dimensional implant geometry data configured to guide an additive manufacturing operation.

In yet another embodiment of the present disclosure, a computer system for designing a patient-specific implant includes at least one computer memory that is not a transitory signal, the at least one computer memory including instructions executable by at least one processor for obtaining or uploading computed tomography (CT) data from a spine of a subject, converting the computed tomography (CT) data into a three-dimensional image, selecting or indicating selected segments of the spine for applying surgical correction, applying one or more correction guidelines for the selected segments of the spine, determining whether the selected segments of the spine conform to the one or more correction guidelines, and generating three-dimensional implant geometry data configured to guide an automated manufacturing operation configured to produce an implant.

In still another embodiment of the present disclosure, a patient-specific implant is manufactured by a process including obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide an additive manufacturing operation.

In yet another embodiment of the present disclosure, a patient-specific implant is manufactured by a process including obtaining image data of a region of interest of the spine of a patient, measuring one or more geometric characteristic of the region of interest from the image data, comparing a measurement obtained for each member of a selected group of the one or more geometric characteristics to a mathematical rule associated with the particular geometric characteristic, creating a corrected value for any of the one or more geometric characteristics that do not conform with the associated mathematical rule, and generating three-dimensional implant geometry data configured to guide an additive manufacturing operation.

In still another embodiment of the present disclosure, a patient-specific implant is manufactured by a process including obtaining or uploading computed tomography (CT) data from a spine of a subject, converting the computed tomography (CT) data into a three-dimensional image, selecting or indicating selected segments of the spine for applying surgical correction, applying one or more correction guidelines for the selected segments of the spine, determining whether the selected segments of the spine conform to the one or more correction guidelines, and generating three-dimensional implant geometry data configured to guide an automated manufacturing operation configured to produce an implant.

DETAILED DESCRIPTION

A patient-specific implant and an efficient method of producing the patient-specific implant are described in the embodiments herein. Patient-specific implants according to embodiments described herein may include interbody devices that have been custom-made to not only correspond with the particular anatomy of a patient, including shape and size, but also, to impart a particular type of correction to the patient. The term "interbody device," as used herein, refers generally to any interbody implant device (interbody device, interbody implant, interbody cage, fusion cage, or spine cage). The interbody devices are typically intended to be placed between two vertebral bodies. Oftentimes, the intervertebral disc is removed prior to the placement of the interbody device. The lower side of an interbody device is intended to abut at least a portion of an upper side (endplate) of a first vertebral body and the upper side of the interbody device is intended to abut at least a portion of a lower side (endplate) of a second vertebral body.

Insufficient contact and load transfer between the vertebral body and the interbody device can produce excessive load transfer in particular locations that can lead the cage to settle or subside into the vertebral body. Furthermore, insufficient contact area or pressure differentials between the interbody device and the vertebral bodies can produce micro-motions and/or macro-motions that can increase subsidence and result in expulsion of the interbody device from the disc space. It is believed by some that this insufficient contact area is due in part to the anatomical variability in the curvature of the vertebral endplates from vertebral level to vertebral level and from patient to patient. Additionally, low bone mineral density index or overaggressive decortications of the endplate can reduce the strength of the endplate and the ability to transfer load from one vertebral body to another. To reduce or eliminate these risks, surgeons carefully prepare the opposing vertebral endplates and attempt to insert an interbody device having as large a footprint (coverage area) as possible, in order to maximize the contact area of the interbody device on the vertebral endplates. When appropriate, the surgeon also places the interbody device on the apophyseal rings to provide as much support and load transfer as possible for spinal distraction, while also ensuring that the interbody device is securely nested within the disc space.

Pre-operative planning software may be utilized to determine or produce implants for surgery. There are two types of pre-operative planning software, those that are device specific and those that are device agnostic. Device specific pre-operative planning software typically provides a method to convert image data, such as CT (computed tomography) scan data, MRI (magnetic resonance induction) data, or x-ray data into two-dimensional or three-dimensional data. The converted data is then used to take measurements of the orthopedic problem (e.g., spine deformity), and to recommend one or more stock or standard model implants for treating the patient. One problem with this strategy is that treatment of the patient is limited to only the device models or sizes that are currently provided by medical device manufacturers. Oftentimes, none of the available models or sizes is appropriate for a particular patient and surgery plan. Complex or large corrections of the spine are typically not possible with the current state of the art in stock implants and device specific pre-operative planning software.

Device agnostic pre-operative planning software is typically used by a medical device manufacturer of a medical professional to provide a custom implant solution for a single patient. Software of this type often provides a method for converting image data (e.g., CT scan, etc.) to three-dimensional data that can be used to measure the orthopedic problem (e.g., spine deformity). Typically, a medical professional works in conjunction with a medical device manufacturer and the applicable regulatory body or controlling organization (FDA, IRB, etc.) to develop a custom device to treat the patient. While this process provides a personalized implant solution, it is an expensive and time-consuming process that is not feasible for most patients, medical professionals, or hospital payer systems.

The systems and methods described herein are configured to provide a three-dimensional shape that represents the ideal implant to fit into the negative space of the spine, once the spine receives the appropriate manipulation in the coronal, sagittal, and axial planes. In other words, the custom shape of the implant will at least partially provide and maintain the desired correction to the spine. Thus, the coronal, sagittal, and axial plane deformities of the spine are corrected, allowing restoration of the anatomical function of the spine. The correction may include both rotation and/or linear displacement along the degrees of freedom. For example, positive displacement along the x-axis, negative displacement along the x-axis, positive rotation around the x-axis, negative rotation around the x-axis, positive displacement along the y-axis, negative displacement along the y-axis, positive rotation around the y-axis, negative rotation around the y-axis, positive displacement along the z-axis, negative displacement along the z-axis, positive rotation around the z-axis, negative rotation around the z-axis. The systems and methods described herein utilize software that is configured to confirm conformity within the validated and regulatory cleared parameters. Upon software verification of the particular design of the interbody device, the software is then configured to capture patient specific data to complete the prescription and transmit the three-dimensional shape and prescription data to the medical device manufacturer. In some embodiments, the hospital or medical facility utilizing the software may itself be the medical device manufacturer. The systems and methods described herein further provide for the manufacture of the implant according to the specifics defined by the software-provided prescription, for example, by additive manufacturing techniques such as three-dimensional printing, or even by subtractive manufacturing techniques, such as CNC-manufacturing. Thus, the turn-around time and the expense, are similar to those for conventional stock implants, although the implants being provided are patient-specific. The patient has the combined benefit of a personalized implant treatment with a conventional price point and a short lead time. There is flexibility, combined with simplicity. The patient's ideal anatomical correction is coded into the prescription and the geometry of the ideal device is sent to a medical device manufacturer for fabrication, or may even be fabricated by a lab in the hospital or other medical treatment site, or remote site.

Figure 1:
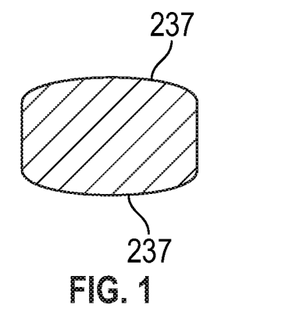
FIGS. 1-22 illustrate a variety of implants configured as intervertebral bodies and spacers, bone plates, pins, dowels, and the like, according to embodiments of the present disclosure.
Figure 2:
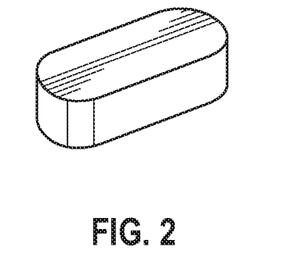
Figure 3:
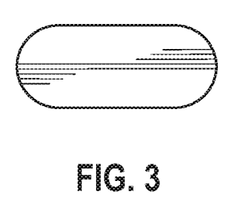
Figure 4:
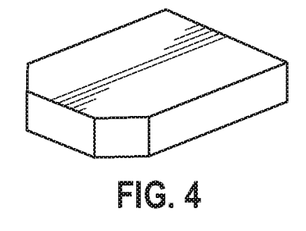
Figure 5:
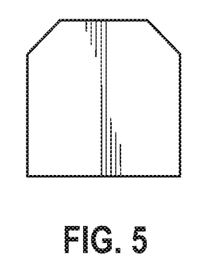
Figure 6:
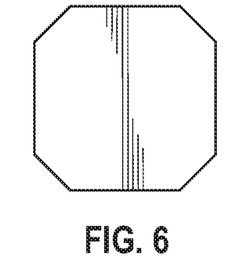
Figure 7:
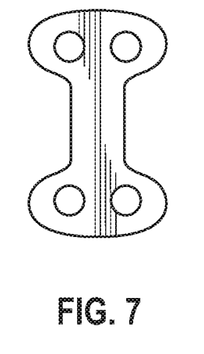
Figure 8:
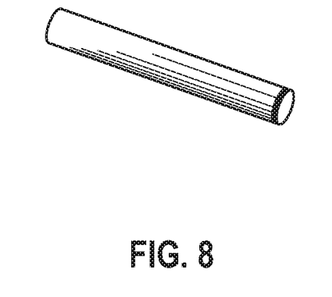
Figure 9:
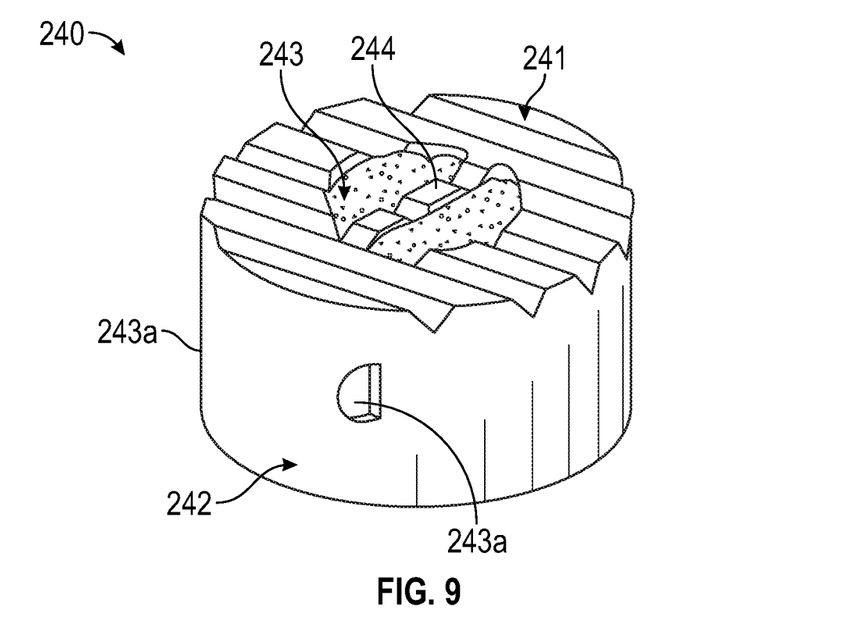
Figure 10:
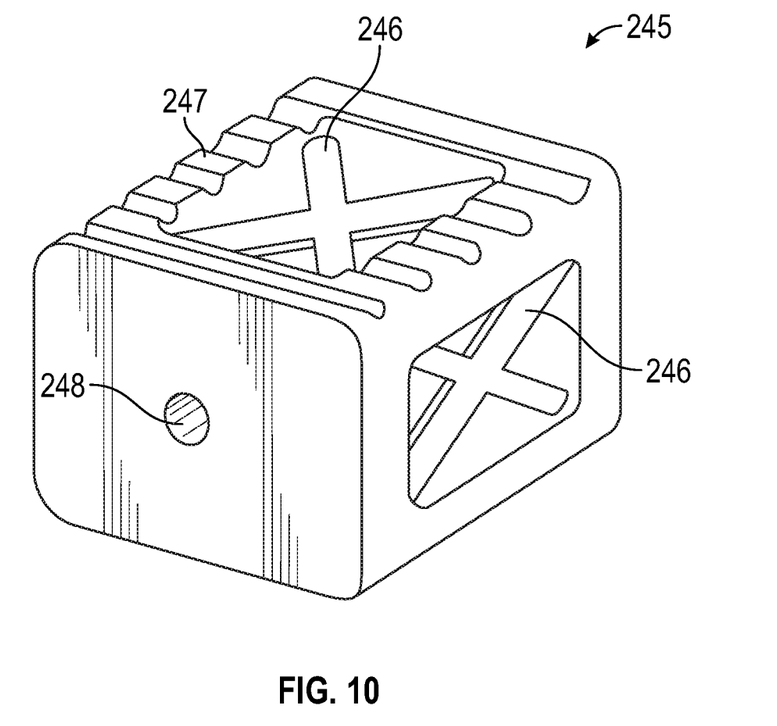
Figure 11:
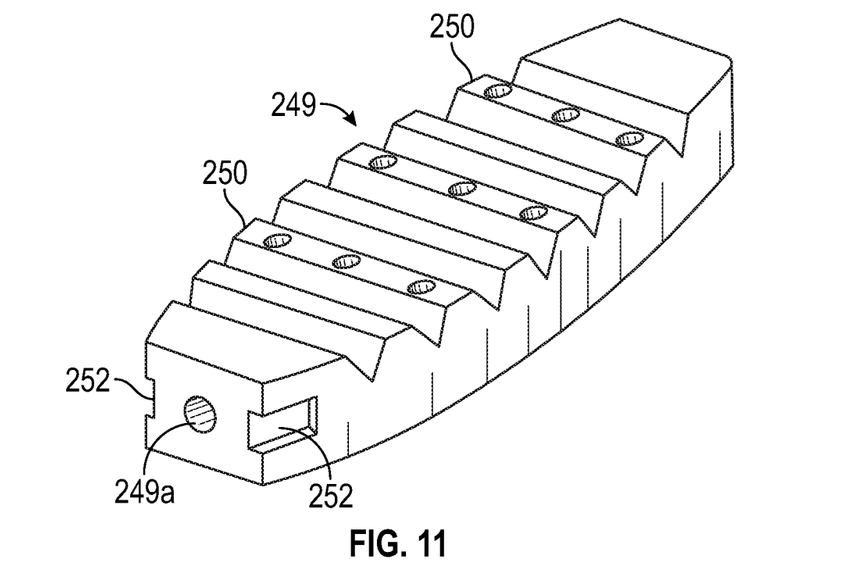

FIGS. 1-22 illustrate a variety of implants which may be produced by the systems and methods described herein, according to several embodiments of the present disclosure. FIG. 1 illustrates an intervertebral implant possessing biconvex surfaces 237 which are configured to match the curvatures of the vertebral endplates with which they come into contact. The biconvex surfaces 237 may each curve laterally (left to right), or curve anteriorly-posteriorly, or curve both laterally and anteriorly-posteriorly (e.g., a hemisphere or other three-dimensional convex shape). FIGS. 2-6 show various views of implants that are suitable for interbody use, including the oval footprints of FIGS. 2-3, the hexagonal footprints of FIGS. 4-5, or the octagonal footprint of FIG. 6. In some embodiments, other polygonal footprints may be utilized. In some embodiments, the footprint may comprise sides that are equal in length to each other, or in other embodiments, all of the sides may be equal in length to each other, or in other embodiments, none of the sides may be equal in length to each other. FIG. 7 shows a cervical bone plate for the fixation of adjacent cervical vertebrae. The bone plate spans two or more vertebrae, but does not necessarily fill the space between two vertebral endplates. The size and shape of the bone plate of FIG. 7, including the location of holes for screws, may be configured to maintain the cervical vertebrae in a particular relation to each other. FIG. 8 illustrates a cylindrical pin or dowel which may be keyed (not shown) to facilitate its installation. FIG. 9 illustrates an intervertebral implant 240 having a textured surface 241, e.g., roughenings, knurlings, ridges, and the like, to resist backing-out of the implant following its insertion in the intervertebral space. Surfaces 241 may converge to provide an anterior ramp configuration possessing a suitable lordotic angle or the surfaces may be essentially flat. The outer profile 242 of the implant can be round, oval, square, diamond-shaped, octagonal, hexagonal, etc., as requirements suggest. The implant can be provided with an opening 243 for receiving a quantity of osteogenic/osteoinductive material and/or a rigid reinforcing member 244 for added strength. The walls of the implant possess a pair of inserter instrument interfaces 243a (only one shown) for engagement with one end of an insertion tool. FIG. 10 depicts an open, or cage-like, structure 245 suitable for use as an anterior or posterior intervertebral implant. Cross braces 246 on one or more sides of the implant provide increased structural strength over that of a totally open configuration. The open space can be advantageously filled with an osteogenic/osteoinducting material. Texturized surfaces, e.g., ridges, 247 are provided to resist backing-out of the implant following its installation. Inserter interface 248 is intended to receive the distal (working end) of an implant insertion tool. FIG. 11 illustrates an intervertebral implant 249 possessing a position-retaining textured surface 250 (ridges) and a pattern of orifices communicating with the interior which possesses a void structure. The sides of the implant at one end thereof have a matching pair of implant inserter interfaces 252 which are intended to be grasped by an insertion tool. One end of the implant possesses an orifice 249a through which an osteogenic/osteoinductive material can be introduced into the interior void communicating channels of the implant.

Figure 12:
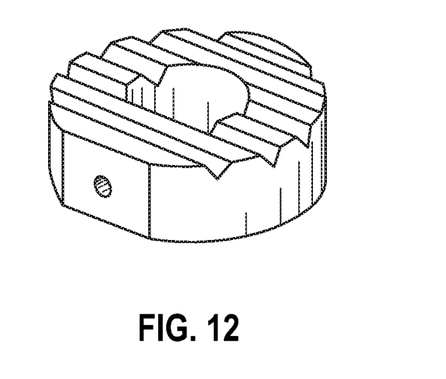
Figure 13:
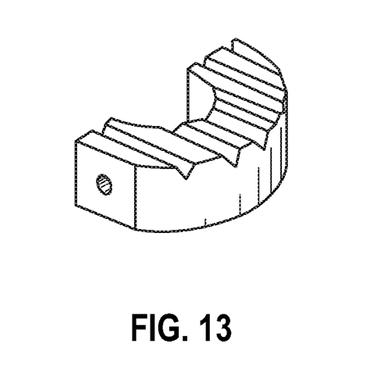
Figure 14:
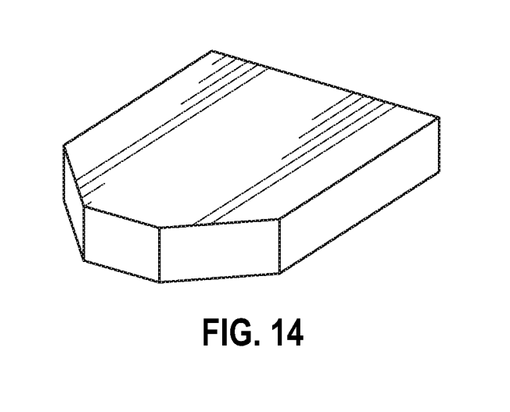
Figure 15:
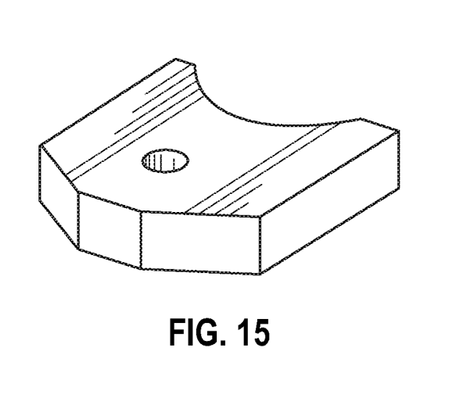
Figure 16:
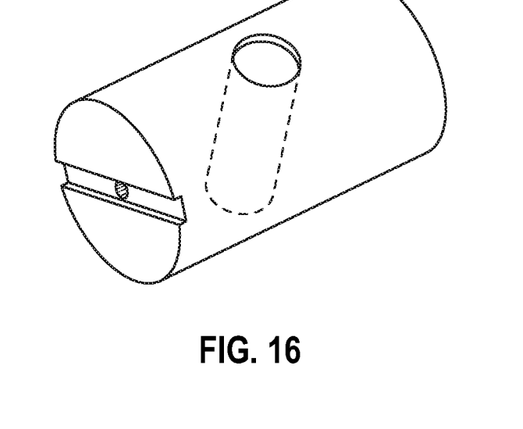
Figure 17:
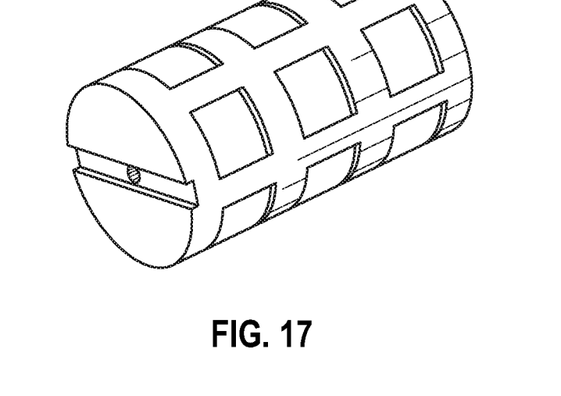
Figure 18:
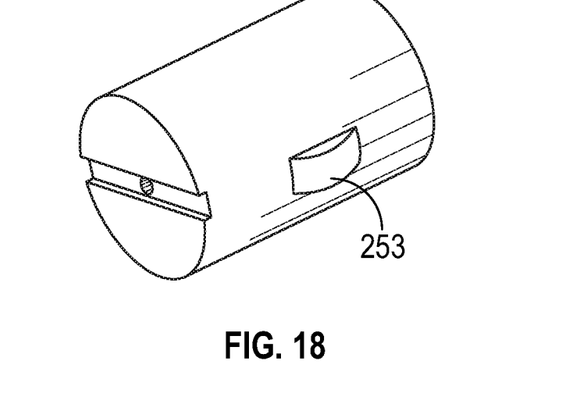
Figure 19:
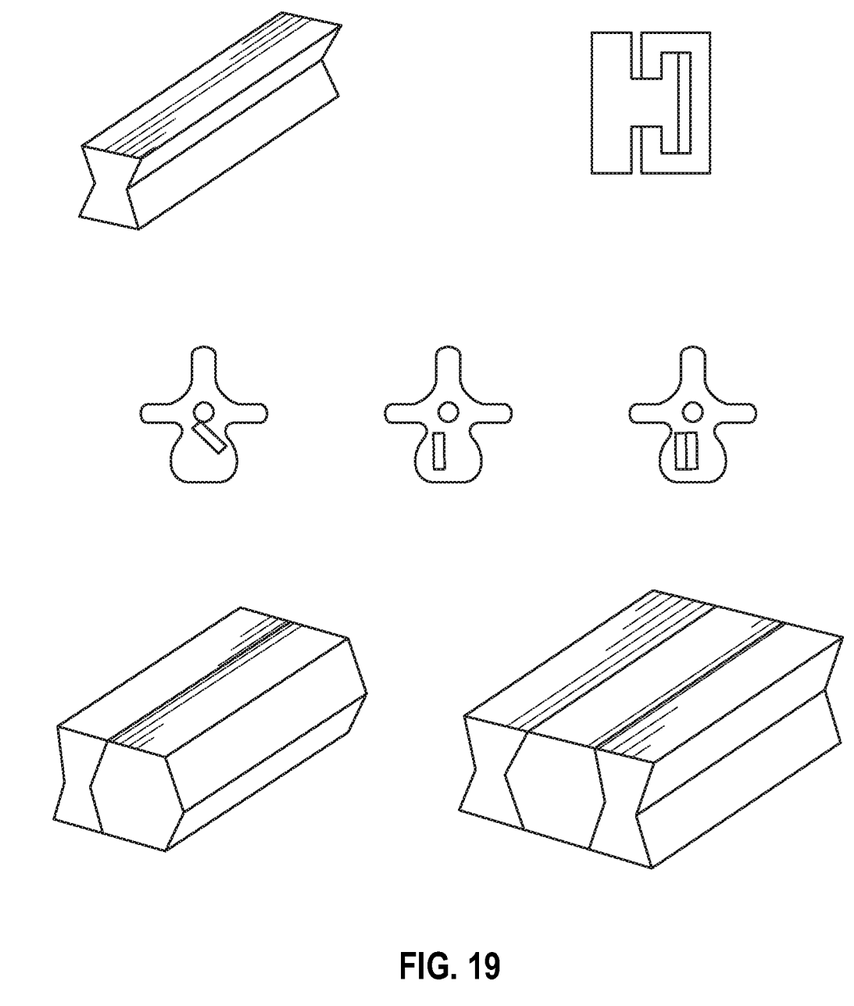
Figure 20:
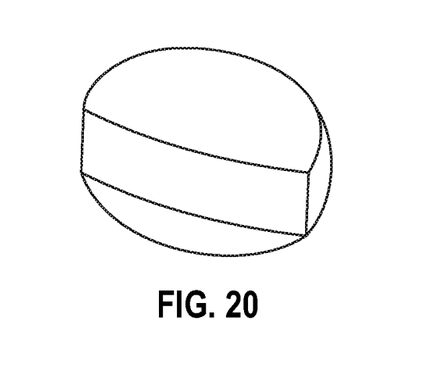
Figure 21:
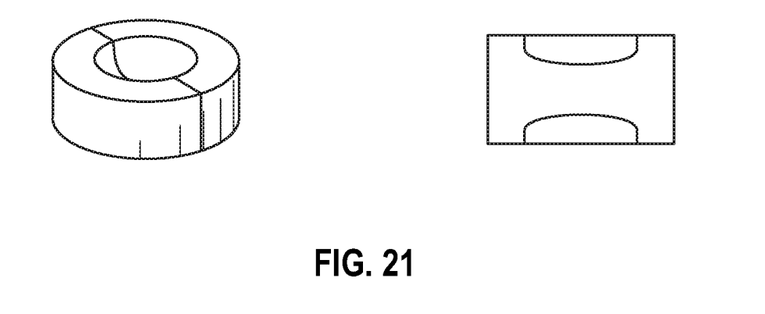
Figure 22:
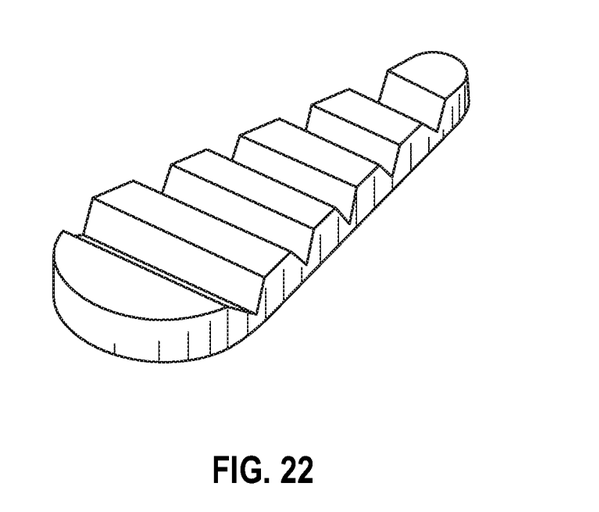

FIGS. 12-15 show various additional configurations of implants for insertion in the intervertebral space: FIG. 12 (an anterior ramp implant), FIG. 13 (a posterior ramp implant), FIG. 14 (a cervical spacer) and FIG. 15 (a cervical spacer including a radiused recess at one side). FIGS. 16-18 show various implants configured as intervertebral dowels. The implant of FIG. 16 is a solid structure with a through bore for receiving osteogenic/osteoinductive material. The implant of FIG. 17 possesses an open, or cage-like, structure which can be packed with osteogenic/osteoinductive material. The implant of FIG. 18 possesses at least one wing-like structure 253 on its longitudinal surface which prevents rotational displacement within the intervertebral space. Each of implants 16-18 possesses a slot and central hole for receiving the distal end of an insertion tool. FIG. 19 illustrates a transforaminal lumbar interbody fusion (TLIF) implant and its assembly from subunits. The implant of FIG. 19 may alternatively be used as a posterior lumbar interbody fusion (PLIF) implant. FIG. 20 depicts a convex anterior interbody ramp with openings communicating with the interior. FIG. 21 shows another embodiment of anterior interbody implant. FIG. 22 shows a solid anterior interbody implant presenting a large surface area for implant-vertebral endplate contact.

Figure 23:
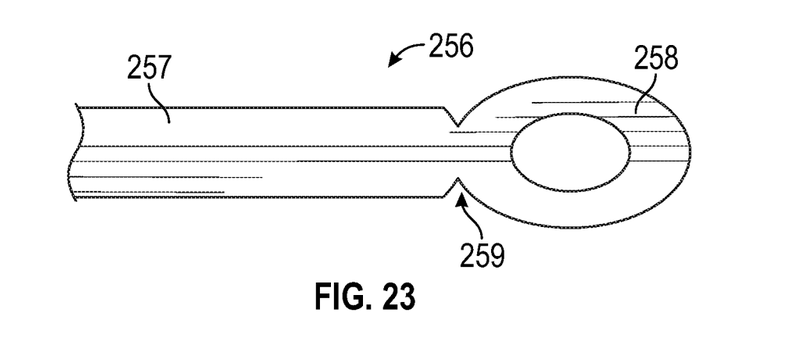
FIG. 23 illustrates the distal end of an integral implant insertion instrument and implant, according to an embodiment of the present disclosure.

FIG. 23 schematically illustrates in plan view the distal end 257 of an integral, or combined, implant insertion instrument and implant 256 wherein implant portion 258 specifically, an intervertebral implant, is joined to the distal end 257 of the instrument portion through a weakened, or break-away, site of attachment 259. Following insertion of the intervertebral implant in the intervertebral space, application of a sharp upward or downward movement of the implant insertion instrument will result in the distal end of the instrument cleanly breaking away, and separating from, the implant which remains in place. Alternatively, the site of attachment 259 may comprise any mechanism that allows the distal end 257 to releasably grip or maintain the implant 258, including, but not limited to: a clamp, an adhesive, epoxy, or hot melt attachment, a magnetic connection, a snap, a threaded attachment, a tapered attachment, a spring attachment, and a combination of any two or more of these attachment features. Custom instruments may even be produced by the systems and methods described herein. For example, a particular patient may have a deformity which requires an instrument having a particular angle that is not available in off-the-shelf instruments.

Figure 24:
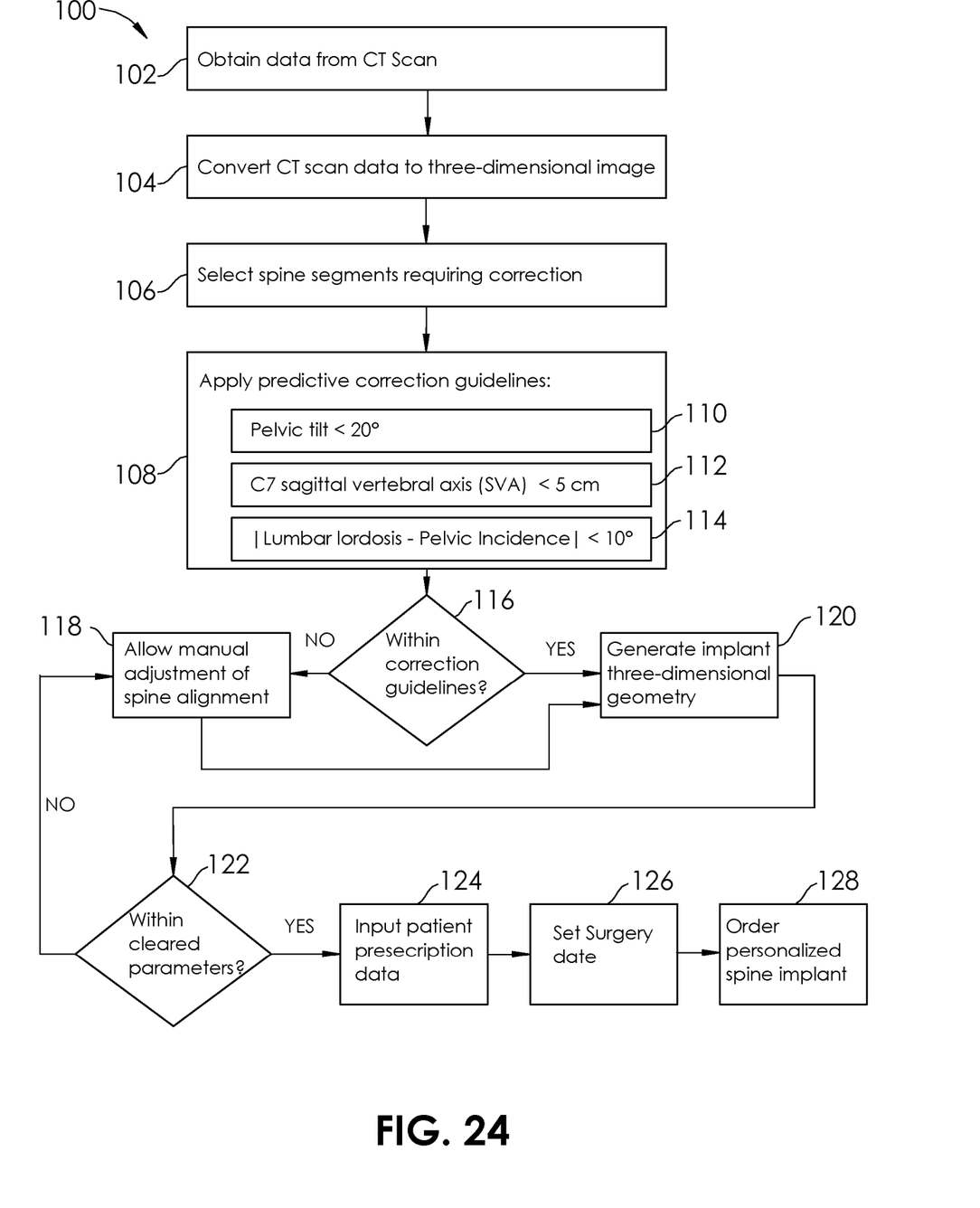
FIG. 24 is a flow chart of a method utilizing a system according to an embodiment of the present disclosure.

FIG. 24 illustrates a method 100 for utilizing a system for producing patient-specific implants. In step 102 scan data is obtained from a CT scan of a patient, for example, a CT scan that includes the spine of the patient, or at least the portion of interest in the spine. In other embodiments the scan data may comprise MRI scan data or x-ray data. In step 104, the CT scan data is converted into a three-dimensional image through software manipulation of the data. Typically, CT scan data is presented in a DICOM format, which includes individual slices of imaging data. A common slide thickness is one mm, though other thickness may be used, such as 0.25 mm, 0.5 mm, 1.5 mm, 2.0 mm, 2.5 mm, 3.0 mm and greater thicknesses. In step 106 spine segments may be selected for analysis. For example, a user interface that is associated with least one computer memory that is not a transitory signal and which comprises instructions executable by at least one processor may be utilized to select a region of interest. In some cases, the region of interest may be a diseased or deformed portion of the spine, including a particular number of successive vertebrae and their surrounding soft tissue. In some cases, the entire spine may be selected. In some cases, only sacral and lumbar vertebrae and their surrounding soft tissue are selected. In some cases, only lumbar and thoracic vertebrae and their surrounding soft tissue are selected. In some cases, only cervical vertebrae and their surrounding soft tissue are selected.

Figure 32:
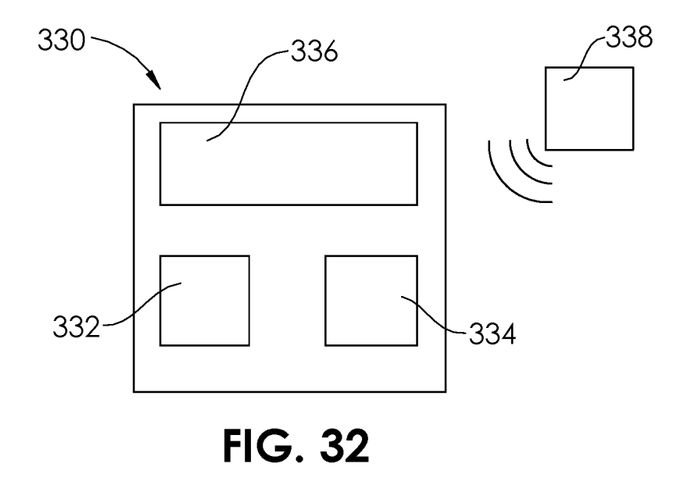
FIG. 32 is a plan view of a computer system, according to an embodiment of the present disclosure.

Turning to FIG. 32, a system 330 containing a memory 332 and a processor 334 may include any number of custom stand-alone devices, or any mobile device, such as an iPhone, smart phone, iPAD, smart watch, laptop or desktop computer. The system 330 may also include a user interface 336. The system 330 may also be configured to access the memory 332 remotely, for example, via internet browser access or other wireless means 338. The three-dimensional image can be converted into a form such that it can be manipulated by a user to measure anatomical deformities related to the disease (e.g., spine disease). The information can then be used by a medical professional, or technical or engineering professional in conjunction or collaboration with a medical professional, to design the optimized geometry of the corrected spine, thus allowing the design of an implant to treat the particular disease or malady.

Figure 25:
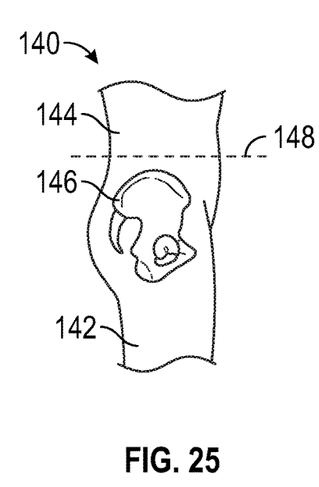
FIG. 25 is a side view of a patient with a neutral pelvis.
Figure 26:
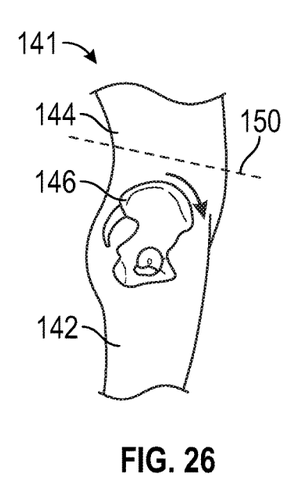
FIG. 26 is a side view of a patient with anterior pelvic tilt.
Figure 27:
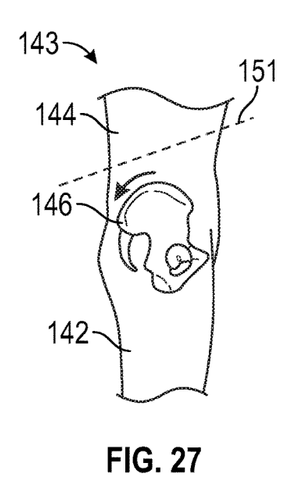
FIG. 27 is a side view of a patient with posterior pelvic tilt.
Figure 28:
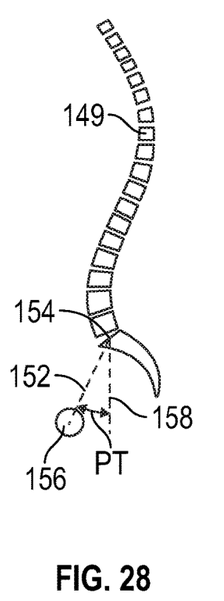
FIG. 28 is a side view of a pelvic tilt angle (PT) in a spine.

In step 108, the computer memory is utilized to apply one or more predictive correction guidelines to the spine or to the selected portion of the spine, or at least a section thereof. A number of predictive correction guidelines may be utilized, but in one embodiment a set of three predictive guidelines is applied, relating to pelvic tilt 110, sagittal alignment 112, and lumbar lordosis 114. Legs 142 and torso 144 of a standing patient 140 are shown in FIG. 25. The patient 140 has a pelvis 146 that is in a neutral condition in relation to horizontal line 148. FIG. 26 illustrates a standing patient 141 who has an anterior pelvic tilt, with forwardly rotated pelvis 146 indicated by curved arrow and line 150 that is angled in relation to horizontal line 148. FIG. 27 illustrates a standing patient 143 who has a posterior pelvic tilt, with backwardly rotated pelvis 146 indicated by curved arrow and line 151 that is angled in relation to horizontal line 148. A spine 149 of a patient is shown in FIG. 28. A pelvic tilt angle PT is the angle created by the vertical axis 158 and a line 152 running from a midpoint of the sacral end plate 154 to the center 156 of the bifemoral heads. The predictive guideline regarding pelvic tilt 110 is defined by the equation wherein the pelvic tilt angle PT is less than 20 degrees (PT<20°). In some embodiments, the predictive guideline regarding pelvic tilt 110 may be defined by the equation 0°<PT<20°.

Figure 29:
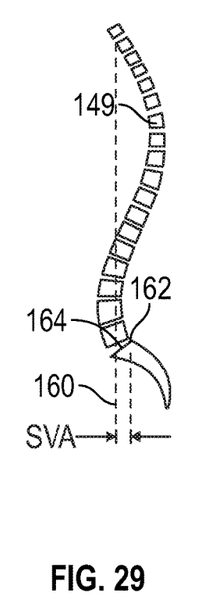
FIG. 29 is a side view of C7 sagittal vertebral axis (SVA) in a spine.

FIG. 29 illustrates a spine 149 having a positive C7 sagittal vertebral axis SVA. The C7 sagittal vertebral axis SVA is the distance from the plumb line 160 dropping from the center of the C7 vertebra to the posterior edge 162 of the upper sacral endplate surface 164. The predictive guideline regarding C7 sagittal vertebral axis (SVA) 112 is defined by the equation wherein the a C7 sagittal vertebral axis (SVA) less than 5 cm (SVA<5 cm). In some embodiments, the predictive guideline regarding the C7 sagittal vertebral axis (SVA) is defined by the equation wherein the absolute value of the C7 sagittal vertebral axis (SVA) is less than 5 cm (|SVA|<5 cm).

Figure 30:
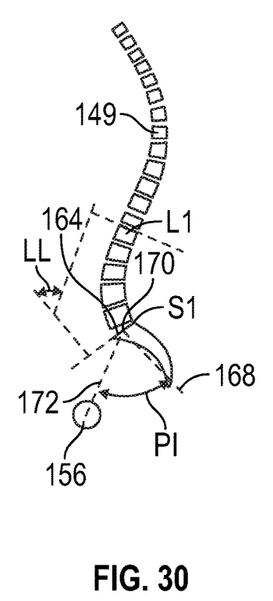
FIG. 30 is a side view of lumbar lordosis (LL) and pelvic incidence (PI) in a spine.

FIG. 30 illustrates a spine 149 with pelvic incidence PI and lumbar lordosis LL indicated. The pelvic incidence PI is the degree of sacral tilt with respect to the pelvis. More specifically, the pelvic incidence PI is the angle between the perpendicular line 168 to the center point 170 of the upper sacral endplate surface 164 and the line 172 between the center point 170 and center 156 of the bifemoral heads. Lumbar lordosis LL is the angle between L1 and S1. The predictive guideline regarding lumbar lordosis 114 is defined by the equation wherein an absolute value of the difference between pelvic incidence PI and lumbar lordosis LL is less than about 10 degrees. More specifically, the predictive guideline regarding lumbar lordosis 114 may be defined by the equation wherein an absolute value of the difference between pelvic incidence PI and lumbar lordosis LL is less than about 9 degrees. In some embodiments, other parameters may be used to formulate alternative or additional corrective guidelines. For example: C2-C7 angle, which evaluates the degree of cervical lordosis, and is the angle between the upper endplate surface of the C2 vertebra and the lower endplate surface of the C7 vertebra; thoracic kyphosis T1-T12 angle, which is the angle between the upper endplate surface of the T1 vertebra and the lower endplate surface of the T12 vertebra; thoracic kyphosis T4-T12 angle, which is the angle between the upper endplate surface of the T4 vertebra and the lower endplate surface of the T12 vertebra; C7 slope angle, which may predict cervical lordosis and thoracic kyphosis, and which is the angle between a horizontal line and the upper endplate surface of the C7 vertebra; sacral slope, which is the angle between a horizontal lune and the slope of the upper sacral endplate surface. Sacral slope SS may have a correlation between with pelvic incidence PI and pelvic tilt PT, such that SS≈PI−PT.

In decision point 116, the computer memory is utilized to determine whether, in the current state of the spine provided by the three-dimensional image, the predictive guidelines 110, 112, 114 are achieved. If one or more of the predictive guidelines 110, 112, 114 are not true for the spine segments selected, then a user may utilize a user interface to adjust spine alignment, as shown in step 118. For example, if the pelvic tilt is determined to be 20° or greater, a user may input or toggle an adjustment that changes the amount of correction in order to achieve a pelvic tilt less than 20°. If it is determined that the predictive guidelines are all achieved (whether user adjustment was or was not required), the system generates three-dimensional geometry in step 120. The three-dimensional geometry may in some cases define a single interbody device, or in other cases may define several interbody devices. In some cases, the three-dimensional geometry may define one or more interbody devices for a single level of the spine, or in other cases may define one or more interbody devices from two or more levels of the spine. In one embodiment, the DICOM data creates a point cloud map, which is then converted to multiple interconnected triangles to create a surface mesh. Based on known density discrepancies between bone and tissue, the three-dimensional mesh surface is parsed for bone surface data and converted to a three-dimensional image with volume. The converted data is saved into memory with a readable file format, such as .STL, .OBJ, or other CAD (computer-aided design) readable file format. In this CAD readable file format, the individual spine vertebral bodies can be isolated and manipulated in the axial, coronal, and sagittal planes.

After the three-dimensional geometry is generated, the system checks in decision point 122 whether the particular correction is within cleared parameters. For example, within a particular amount of correction that is approved under a regulatory clearance; or, within a particular amount of correction that is approved under an IRB-controlled or FDA-controlled clinical trial. In addition to, or instead of, the amount of correction, other parameters may determine whether the three-dimensional geometry performs within cleared parameters in decision point 122. For example, the total volume or total mass of the implant(s) may be controlled, such that it must be within a particular range, or that it must be below a certain amount per unit weight of patient. If the correction (or other parameters) is not within the cleared range(s), user-initiated input may be performed, as in step 118. In some embodiments, the system may suggest the amount to adjust each parameter of spine alignment, allowing the user to accept this suggestion, or to choose a different value of change. In some cases, step 122 may not be necessary, for example, when certain procedures do not have implant-based regulatory limitations. A particular manner of validating a cleared amount of correction, is to check the three-dimensional envelope of the spine implant at both the maximum material condition and the least material condition. For example, an FDA clearance may take into account both of these conditions, in one or more patient indications.

Once the three-dimensional geometry is accepted by the user, and, if applicable, by the limitations of step 122, a patient prescription can be created in step 124. The patient prescription may comprise one or more three-dimensional files that are used in additive manufacturing, including, but not limited to: .AMF, .X3D, Collada (Collaborative Design Activity), .STL, .STP, .STEP, or .OBJ. The patient prescription may alternatively comprise one or more three dimensional files, including, but not limited to: .IGS, .STP, .STEP, .3ds, .blend, .dae, .ipt, .skp, .fbx, .lwo, .off, .ply, .sldprt, .sldasm, and .X_T. In some cases, the patient prescription may also include one or more two-dimensional files, for example, to map or guide the surgical treatment, or to stage the utilization of each implant. The two-dimensional files may include, but are not limited to: .dwg, .dwf, .dxf, .pdf, or .acis. The surgery can be scheduled in step 126, and the personalized implant can be ordered in step 128.

The step 128 may include using the three-dimensional files to manufacture the implant using one or more additive manufacturing or subtractive manufacturing methods. Additive manufacturing methods include, but are not limited to: three-dimensional printing, stereolithography (SLA), selective laser melting (SLM), powder bed printing (PP), selective laser sintering (SLS), selective heat sintering (SHM), fused deposition modeling (FDM), direct metal laser sintering (DMLS), laminated object manufacturing (LOM), thermoplastic printing, direct material deposition (DMD), digital light processing (DLP), inkjet photo resin machining, and electron beam melting (EBM). Subtractive manufacturing methods include, but are not limited to: CNC machining, EDM (electrical discharge machining), grinding, laser cutting, water jet machining, and manual machining (milling, lathe/turning).

Following the manufacture of the implant, a bone-friendly scaffold is created for fusion to one or more vertebrae. The implant may comprise one or more of the following materials: titanium, titanium alloy, titanium-6AL-4V, tantalum, and PEEK (polyether ether ketone). The implant may also comprise/be coated with a biologic material. Examples of potential biological materials include, but are not limited to: hydroxylapetite (hydroxyapetite), recombinant human bone morphogenic proteins (rhBMP-2, rhBMP-7), bioactive glass, beta tri-calcium phosphate, human allograft (cortical and/or cancellous bone), xenograft, other allograft, platelet rich plasma (PRP), stem cells, and other biomaterials. In addition, synthetic ceramics having osteogenic properties may be utilized. The manufacture of the implant may be further guided by patient information, including patient age, patient weight, or prior patient surgical history. For example, a patient with a high BMI (body mass index) can require a stiffer or stronger implant, such as an implant made with a different material (e.g., having mechanical characteristics) and/or an implant having thicker material cross-sectional dimensions. The lattice structure forming the implant can be optimized to meet the patient's biomechanical needs for stability. Additionally, a patient with a low BMI and/or with osteoporotic bone or osteopenia can benefit from an implant having lower stiffness (higher flexibility), thus helping to reduce the risk of subsidence. Furthermore, a patient having a previously failed fusion may be at risk for adjacent level disc disease and/or proximal joint kyphosis. An implant can be tailored to alleviate this particular situation.

Figure 31:
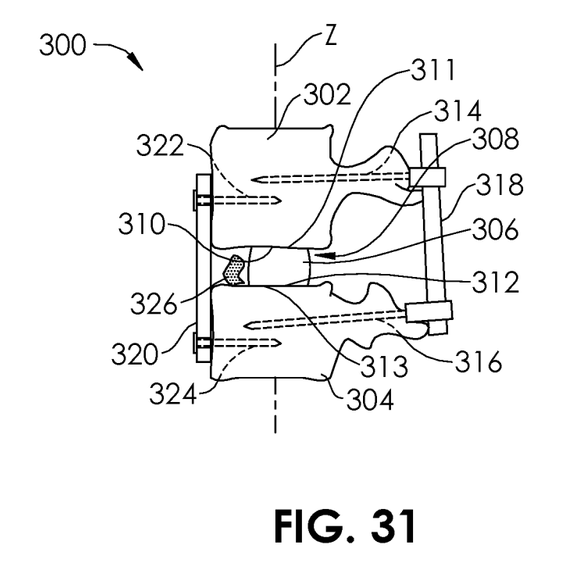
FIG. 31 is a side view of an interbody device implanted between two vertebrae of a patient.

FIG. 31 illustrates a portion of a spine 300 including a first vertebra 302 and a second vertebra 304. In use, a patient-specific interbody device 306 manufactured using according to the embodiments described herein is placed by a user into the negative space 308 of the spine 300, and engaged between a lower endplate surface 310 of the first vertebra 302 and an upper endplate surface 312 of the second vertebra 304. An upper surface 311 of the interbody device 306 engages the lower endplate surface 310 of the first vertebra 302 and a lower surface 313 of the interbody device 306 engages the upper endplate surface 312 of the second vertebra 304. The interbody device 306 is configured to maintain the distance between the first vertebra 302 and the second vertebra 304, and more specifically, between the lower endplate surface 310 of the first vertebra 302 and the upper endplate surface 312 of the second vertebra 304 (e.g., along the Z-axis). The interbody device 306 may also be configured to maintain X-axis and/or Y-axis position (not shown) between the first vertebra 302 and the second vertebra 304, and may be configured to maintain rotational orientation of one of both of the first vertebra 302 and the second vertebra 304, for example, in relation to the X-axis, Y-axis, and/or Z-axis. In some embodiments, pedicle screws 314, 316 and a rod 318 may be used to further lock the orientation in place. In other embodiments, a plate 320 and screws 322, 324 may be used to further lock the orientation in place. Though both the rod 318 and plate 320 are shown coupled to the first vertebra 302 and the second vertebra 304 in FIG. 31, commonly only one of two would be used, though it is possible to incorporate both in certain situations. Bone graft 326 or other biological materials may be used to further promote fusion of the first vertebra 302 and the second vertebra 304, and may be implanted within the negative space 308.

The systems and methods described herein may be utilized to correct other physiological ailments requiring a patient-specific implant. For example, wedge-shaped implants for maintaining wedge osteotomies in the spine, or other orthopedic areas such as the hip, jaw, chin or knee for arthritic or non-arthritic conditions, may be designed with the teachings of the present disclosure. Particular procedures include: high tibial osteotomy (tibia), distal femoral osteotomy (femur), Evans wedge or Cotton wedge (foot and ankle).

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

While embodiments have been shown and described, various modifications may be made without departing from the scope of the inventive concepts disclosed herein.

What is claimed is:

1. A computer-implemented method for designing a patient-specific implant, comprising:
   obtaining image data of a region of interest of a spine of a patient;
   generating a first virtual model depicting patient anatomy in the region of interest;
   receiving, from a user, one or more adjustments to the patient anatomy depicted in the first virtual model, wherein the one or more adjustments correspond to a desired surgical correction;
   generating a second virtual model depicting the adjusted patient anatomy;
   causing the second virtual model to be displayed to the user;
   measuring one or more geometric characteristics of the adjusted patient anatomy from the second virtual model;
   determining whether a measurement obtained for at least one of the one or more geometric characteristics of the adjusted patient anatomy conforms to a mathematical rule for one or more predictive anatomical corrections and associated with the at least one geometric characteristic; and
   generating three-dimensional implant geometry data based on the image data if the measurement of the at least one of the one or more geometric characteristics conforms with the associated mathematical rule, the implant geometry data configured to guide an additive manufacturing operation to manufacture a patient-specific implant configured to provide the adjusted patient anatomy when implanted in the patient.

2. The method of claim 1, further comprising creating a corrected value for the at least one of the one or more geometric characteristics if the measurement of the at least one of the one of more geometric characteristics does not conform with the associated mathematical rule.

3. The method of claim 2, further comprising generating the three-dimensional implant geometry data if each of a predetermined set or subset of measurements or corrected values of the one or more geometric characteristics conforms with the associated mathematical rule.

4. The method of claim 1, wherein the one or more geometric characteristics comprises pelvic tilt.

5. The method of claim 4, wherein the mathematical rule associated with pelvic tilt is defined by a pelvic tilt angle (PT) between 0 degrees and 20 degrees.

6. The method of claim 1, wherein the one or more geometric characteristics comprises sagittal alignment.

7. The method of claim 6, wherein the mathematical rule associated with sagittal alignment is defined by a C7 sagittal vertebral axis (SVA) having an absolute value less than 5 cm.

8. The method of claim 1, wherein the one or more geometric characteristics comprises lumbar lordosis.

9. The method of claim 8, wherein the mathematical rule associated with lumbar lordosis is defined by an absolute value of the difference between pelvic incidence and lumbar lordosis less than 10 degrees.

10. The method of claim 1, wherein the image data comprises computed tomography (CT) data.

11. The method of claim 1, wherein the image data comprises magnetic resonance imaging (MRI) data.

12. The method of claim 1, wherein the image data comprises x-ray data.

13. The method of claim 1, further comprising forming a patient-specific implant in an additive manufacturing operation guided by the implant geometry data.

14. The method of claim 13, wherein the forming step is further guided by patient information.

15. The method of claim 14, wherein the patient information includes one or more of patient age, patient weight, or prior patient surgical history.

16. The method of claim 13, wherein the patient-specific implant further comprises a biologic material.

17. The method of claim 13, wherein the patient specific implant comprises an interbody device.

18. The method of claim 1, wherein the additive manufacturing operation is an automated manufacturing operation.

19. The method of claim 1, wherein if the measurement of the at least one of the one or more geometric characteristics does not conform with the associated mathematical rule,
(a) allowing modification of the adjusted patient anatomy;
(b) after modification of the adjusted patient anatomy, measuring one or more modified geometric characteristics to obtain a new measurement;
(c) determining whether the new measurement conforms to the mathematical rule;
(d) if the new measurement does not conform with the associated mathematical rule,
repeating (a)-(c) until the respective new measurement conforms with the associated mathematical rule; and
generating three-dimensional implant geometry data based on new image data associated with the one or more modified geometric characteristics and the new measurement that conforms with the associated mathematical rule.

20. The method of claim 1, wherein generating the first virtual model includes converting the image data into a three-dimensional image.

21. The method of claim 20, wherein the three-dimensional image can be manipulated by the user.

22. The method of claim 20, wherein generating the second virtual model includes updating the three-dimensional image to reflect the adjusted patient anatomy.

23. A computer system for designing a patient-specific implant, comprising:
at least one computer memory that is not a transitory signal, the at least one computer memory comprising instructions executable by at least one processor for:
obtaining image data of a region of interest of a spine of a patient;
generating a first virtual model depicting patient anatomy in the region of interest;
receiving, from a user, one or more adjustments to the patient anatomy depicted in the first virtual model, wherein the one or more adjustments correspond to a desired surgical correction;
generating a second virtual model depicting the adjusted patient anatomy;
causing the second virtual model to be displayed to the user;
measuring one or more geometric characteristics of the adjusted patient anatomy from the second virtual model;
determining whether a measurement obtained for at least one of the one or more geometric characteristics of the adjusted patient anatomy conforms to a mathematical rule for one or more predictive anatomical corrections and associated with the at least one geometric characteristic; and
generating three-dimensional implant geometry data based on the image data if the measurement of the at least one of the one or more geometric characteristics conforms with the associated mathematical rule, the implant geometry data configured to guide an additive manufacturing operation to manufacture a patient-specific implant configured to provide the adjusted patient anatomy when implanted in the patient.

24. A patient-specific implant manufactured by a process comprising:
obtaining image data of a region of interest of a spine of a patient;
generating a first virtual model depicting patient anatomy in the region of interest;
receiving, from a user, one or more adjustments to the patient anatomy depicted in the first virtual model, wherein the one or more adjustments correspond to a desired surgical correction;
generating a second virtual model depicting the adjusted patient anatomy;
causing the second virtual model to be displayed to the user;
measuring one or more geometric characteristics of the adjusted patient anatomy from the second virtual model;
determining whether a measurement obtained for at least one of the one or more geometric characteristics of the adjusted patient anatomy conforms to a mathematical rule for one or more predictive anatomical corrections and associated with the at least one geometric characteristic; and
generating three-dimensional implant geometry data based on the image data if the measurement of the at least one of the one or more geometric characteristics conforms with the associated mathematical rule, the implant geometry data configured to guide an additive manufacturing operation to manufacture the patient-specific implant configured to provide the adjusted patient anatomy when implanted in the patient.

25. A computer-implemented method for designing a patient-specific implant, comprising:
   analyzing image data of a region of interest of a spine of a patient, wherein analyzing the image data includes:
      measuring one or more geometric characteristics of the region of interest from the image data, and
      comparing a measured value of at least one of the one or more geometric characteristics to one or more criteria associated with the at least one geometric characteristic,
   if the measured value conforms with the one or more criteria, generating three-dimensional implant geometry data based at least in part on the image data and/or the measured value, wherein the three-dimensional implant geometry data includes a three-dimensional geometry of a patient-specific implant and is configured for use with a manufacturing operation; and
   if the measured value does not conform with the one or more criteria, requiring modification of the geometric characteristic to conform with the one or more criteria before generating the three-dimensional implant geometry data.

26. The method of claim 25, wherein the image data includes a three-dimensional image of the region of interest.

27. The method of claim 25, wherein the image data includes one or more modifications to the region of interest relative to native patient anatomy.

28. The method of claim 25, wherein the criteria includes a predetermined range of values.

29. The method of claim 25, wherein the criteria includes a predetermined threshold.

30. The method of claim 25, further comprising determining whether the patient-specific implant is configured to, when implanted in the patient, provide a correction to the spine of the patient that is within one or more cleared parameters.

* * * * *

UNITED STATES PATENT AND TRADEMARK OFFICE
CERTIFICATE OF CORRECTION

Page 1 of 3

PATENT NO. : 11,083,586 B2
APPLICATION NO. : 16/207116
DATED : August 10, 2021
INVENTOR(S) : Michael J. Cordonnier It is certified that error appears in the above-identified patent and that said Letters Patent is hereby corrected as shown below:

On the Title Page

Delete the title page and substitute therefor with the attached title page consisting of the corrected illustrative figure(s).

In the Drawings

Please replace FIG. 24 with FIG. 24 as shown on the attached page.

In the Specification

In Column 9, Line 7, delete "the a" and insert -- the --, therefor.

In Column 9, Line 7, after "(SVA)" insert -- is --.

In Column 10, Line 61, delete "(SHM)" and insert -- (SHS) --, therefor.

In Column 11, Line 11, delete "hydroxylapetite (hydroxyapetite)," and insert -- hydroxylapatite (hydroxyapatite), --, therefor.

Signed and Sealed this
Twenty-eighth Day of December, 2021

Drew Hirshfeld
*Performing the Functions and Duties of the
Under Secretary of Commerce for Intellectual Property and
Director of the United States Patent and Trademark Office*

(12) United States Patent
Cordonnier

(10) Patent No.: US 11,083,586 B2
(45) Date of Patent: Aug. 10, 2021

(54) SYSTEMS AND METHODS FOR MULTI-PLANAR ORTHOPEDIC ALIGNMENT

(71) Applicant: CARLSMED, INC., Carlsbad, CA (US)

(72) Inventor: Michael J. Cordonnier, Carlsbad, CA (US)

(73) Assignee: Carlsmed, Inc., La Jolla, CA (US)

( * ) Notice: Subject to any disclaimer, the term of this patent is extended or adjusted under 35 U.S.C. 154(b) by 0 days.

(21) Appl. No.: 16/207,116

(22) Filed: Dec. 1, 2018

(65) Prior Publication Data
US 2019/0167435 A1  Jun. 6, 2019

Related U.S. Application Data

(60) Provisional application No. 62/594,510, filed on Dec. 4, 2017.

(51) Int. Cl.
*A61F 2/30* (2006.01)
*A61F 2/44* (2006.01)

(52) U.S. Cl.
CPC ........ *A61F 2/30942* (2013.01); *A61F 2/4455* (2013.01); *A61F 2/446* (2013.01);
(Continued)

(58) Field of Classification Search
CPC .... A61F 2/30942; A61F 2/4455; A61F 2/446; A61F 2/4465; A61F 2/447; A61B 34/20; A61B 34/25; A61B 34/30
See application file for complete search history.

(56) References Cited

U.S. PATENT DOCUMENTS 4,704,686 A  11/1987 Aldinger
6,696,073 B2  2/2004 Boyce et al.
(Continued)

FOREIGN PATENT DOCUMENTS

CN  104318009 A  1/2015
CN  104353121 A  2/2015
(Continued)

OTHER PUBLICATIONS

Endo, Kenji et al. "Measurement of whole spine sagittal alignment using the SLOT radiography of the SONIALVISION safire series clinical application." Medical Now, No. 78; Aug. 2015, 4 pages.
(Continued)

*Primary Examiner* — Si Ming Ku
(74) *Attorney, Agent, or Firm* — Perkins Coie LLP

(57) ABSTRACT

A method for designing a patient-specific implant includes obtaining image data of a region of interest of the spine of a patient, measuring one or more geometric characteristic of the region of interest from the image data, comparing a measurement obtained for at least one of the one or more geometric characteristics to a mathematical rule associated with the particular geometric characteristic, and generating three-dimensional implant geometry data if the measurement of the at least one of the one or more geometric characteristics conforms with the associated mathematical rule, the implant geometry data configured to guide an additive manufacturing operation.

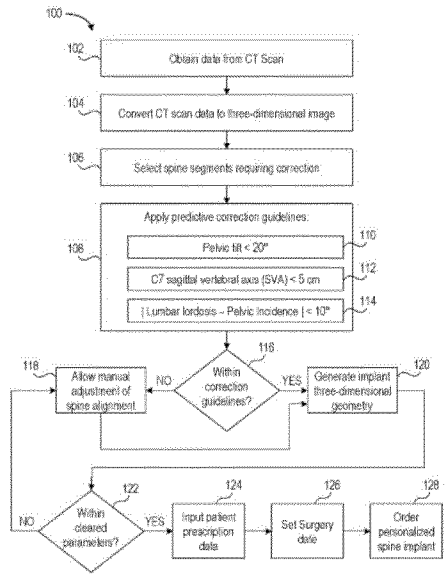

30 Claims, 9 Drawing Sheets